(12) United States Patent
Chen et al.

(10) Patent No.: US 11,350,941 B2
(45) Date of Patent: Jun. 7, 2022

(54) HANDLE ASSEMBLY AND STAPLER INCLUDING THE SAME

(71) Applicant: TOUCHSTONE INTERNATIONAL MEDICAL SCIENCE CO., LTD., Jiangsu (CN)

(72) Inventors: Zhi Chen, Jiangsu (CN); Yi Guo, Jiangsu (CN); Jiang Lin, Jiangsu (CN); Xiaowei Xu, Jiangsu (CN)

(73) Assignee: TOUCHSTONE INTERNATIONAL MEDICAL SCIENCE CO., LTD.

( * ) Notice: Subject to any disclaimer, the term of this patent is extended or adjusted under 35 U.S.C. 154(b) by 148 days.

(21) Appl. No.: 16/957,564

(22) PCT Filed: Dec. 12, 2018

(86) PCT No.: PCT/CN2018/120697
§ 371 (c)(1),
(2) Date: Jun. 24, 2020

(87) PCT Pub. No.: WO2019/128719
PCT Pub. Date: Jul. 4, 2019

(65) Prior Publication Data
US 2020/0315628 A1    Oct. 8, 2020

(30) Foreign Application Priority Data

Dec. 26, 2017  (CN) .......................... 201711434138.2
Dec. 26, 2017  (CN) .......................... 201711435672.5
(Continued)

(51) Int. Cl.
*A61B 17/068*  (2006.01)
*A61B 17/115*  (2006.01)
(Continued)

(52) U.S. Cl.
CPC ........ *A61B 17/1155* (2013.01); *A61B 17/326* (2013.01); *A61B 2017/00367* (2013.01);
(Continued)

(58) Field of Classification Search
CPC ........ A61B 2017/00367; A61B 17/068; A61B 17/115
(Continued)

(56) References Cited

U.S. PATENT DOCUMENTS

| | | | |
|---|---|---|---|
| 5,240,163 A * | 8/1993 | Stein | A61B 17/072 227/175.3 |
| 5,318,221 A * | 6/1994 | Green | A61B 17/07207 227/178.1 |
| 5,782,396 A * | 7/1998 | Mastri | A61B 17/07207 227/175.3 |
| 8,695,866 B2 * | 4/2014 | Leimbach | A61B 17/10 227/175.2 |

(Continued)

FOREIGN PATENT DOCUMENTS

| | | |
|---|---|---|
| CN | 103142278 A | 6/2013 |
| CN | 106388948 A | 2/2017 |

(Continued)

OTHER PUBLICATIONS

Communication regarding corresponding RU 2020124375/14; dated Nov. 20, 2020.
(Continued)

*Primary Examiner* — Gloria R Weeks
(74) *Attorney, Agent, or Firm* — Dickinson Wright PLLC

(57) ABSTRACT

A handle assembly and a surgical stapler including the handle assembly is provided, including a first handle and a second handle, both can rotate around a first pivot pin. Either the first or the second handle is provided with a slider and a sliding slot. When the slider moves from a first section of the sliding slot to a second section, the two handles become
(Continued)

linked. The first handle can still be squeezed even if the stapler has not reached the firing position, but the second handle will not rotate and the stapler will not be fired; featured by the design of two torsion springs and two pivot pins, the first and the second handle are pivotally attached and can be rotated around the same rotation center that remains unchanged in both the insurance position and the firing position, rendering an enhanced stapler structure stability and improved operator experience.

19 Claims, 30 Drawing Sheets

(30) Foreign Application Priority Data

Dec. 26, 2017 (CN) .......................... 201721846890.3
Dec. 26, 2017 (CN) .......................... 201721849675.9

(51) Int. Cl.
*A61B 17/326* (2006.01)
*A61B 17/00* (2006.01)
*A61B 17/072* (2006.01)

(52) U.S. Cl.
CPC ............... *A61B 2017/07257* (2013.01); *A61B 2017/07271* (2013.01); *A61B 2017/07285* (2013.01)

(58) Field of Classification Search
USPC ...................................................... 227/175.2
See application file for complete search history.

(56) References Cited

U.S. PATENT DOCUMENTS

| | | | |
|---|---|---|---|
| 8,733,611 B2 * | 5/2014 | Milliman | A61B 17/068 227/175.2 |
| 9,700,341 B2 * | 7/2017 | Conlon | A61B 17/320068 |
| 9,861,358 B2 * | 1/2018 | Marczyk | A61B 17/07207 |
| 10,441,272 B2 * | 10/2019 | Gustafson | A61B 17/06133 |
| 10,478,189 B2 * | 11/2019 | Bear | H02J 7/00 |
| 2017/0181748 A1 | 6/2017 | Hessler et al. | |

FOREIGN PATENT DOCUMENTS

| | | |
|---|---|---|
| CN | 206261635 U | 6/2017 |
| CN | 107106180 A | 8/2017 |
| CN | 107485429 A | 12/2017 |
| EP | 1908426 A1 | 4/2008 |
| EP | 1908426 A1 | 9/2008 |
| JP | 2009189831 A | 8/2009 |
| JP | 2015503949 A | 2/2015 |
| RU | 2025093 C1 | 12/1994 |
| WO | 2005037084 A2 | 4/2005 |
| WO | 2010048811 A1 | 5/2010 |

OTHER PUBLICATIONS

International Search Report regarding related PCT App. No. PCT/CN2018/120697, dated Feb. 28, 2019.
Office Action regarding corresponding JP App. No. 2020-535540; dated Jun. 22, 2021.
Extended European Search Report regarding corresponding EP App. No. 18894080.3; dated Sep. 3, 2021.

* cited by examiner

HANDLE ASSEMBLY AND STAPLER INCLUDING THE SAME

CROSS-REFERENCE TO RELATED APPLICATIONS

This application is based upon PCT patent application No. PCT/CN2018/120697, filed on Dec. 12, 2018, which claims priority to Chinese Patent Applications No. 201711435672.5, No. 201721849675.9, No. 201711434138.2, and No. 201721846890.3, filed on Dec. 26, 2017, the entire contents of which are incorporated herein by reference.

TECHNICAL FIELD

The present disclosure relates generally to surgical instruments, more particularly, to stapler technology, and specifically to a handle assembly and a stapler including the same.

BACKGROUND

Digestive tract tumor is one of human diseases of high incidence. During treatment, a circular stapler is widely used for suturing physiological tissues such as tissues in the digestive tract, instead of the manual operation by operators. The circular stapler is a common surgical instrument, and used for suturing from end to end, or from end to side of the physiological tissues of esophagus, stomach, intestine, etc., in a way of axial internal stapling. During the process of anastomoses, two sections of tissues are accommodated in the stapler, and form a circular anastomotic stoma after firing the stapler, to rebuild a tissue channel.

In the prior art, the circular stapler includes an instrument body, a handle assembly movably connected to the instrument body and an anvil assembly cooperated with the instrument body. The instrument body includes a cartridge assembly located on a distal end and a knob located on a proximal end thereof. The cartridge assembly includes a circular cartridge and a cutter, and the knob can be rotated relative to the instrument body. In the present disclosure, the positions of the distal end and the proximal end are defined relative to an operator, wherein, the distal end is an end closer to the operator, the proximal end is another end far from the operator and closer to a surgical position. The anvil assembly includes an anvil, an anvil cap on the top of the anvil, a cutter anvil inside the anvil and an anvil shaft detachably connected to the instrument body. During operation, after the tumor tissues are separated and removed, the anvil shaft is connected to the distal end of instrument body through a purse on one end of the tissues, the knob is rotated to shorten a distance between the cartridge and the anvil to an appropriate distance. The stapler is then able to be fired by pressing the handle to accomplish the suturing operation. Along with the development of medical instruments, the circular stapler has been more and more widely used for treatment of diseases such as hemorrhoids.

Meanwhile, in urinary surgical field, another kind of circular stapler is also applied to treat redundant prepuce and phimosis, which is called circumcision stapler. The structure of the circumcision stapler is similar to the circular stapler for digestive tract as aforementioned, except for the glans cap assembly cooperated with the instrument body. Similarly, the glans cap assembly includes an anvil, a glans cap fixedly connected to the anvil, a cutter anvil and a central rod detachably connected to the instrument body. During operation, the prepuce tissues to be cut are fixed to the glans cap, the central rod is configured to the distal end of the instrument body, and the knob is rotated to shorten a distance between the glans gap and the cartridge to an appropriate distance. The stapler is then able to be fired by pressing the handle to accomplish the suturing operation.

Along with the technological development, the firing transmission mechanism of the circular stapler has been improved with a lockout mechanism added. Therefore, when the stapler is not ready to be fired, even the operator presses the handle, the handle cannot be moved for the lockout mechanism, to prevent the stapler from being fired by mistake. However, in practice, the lockout mechanism has some defects. For example, the insurance mechanism has some negative impacts on the operators' experience, and the casing of the stapler may be cracked if the operator presses the handle vigorously.

SUMMARY

In relation to the problems in the prior art, the objective of the present disclosure is to provide a handle assembly and a stapler including the handle assembly. When the stapler is not ready to be fired, a first handle and a second handle are not linked, and the stapler cannot be fired. The two handles share a same rotation center.

The present disclosure provides a handle assembly for firing a stapler, including:
a first handle and a second handle;
a first pivot pin, fixedly secured to a housing of the stapler and passing through the first handle and the second handle;
a first torsion spring, sleeved on the first pivot, and two ends of the first torsion spring respectively engaged with the housing of the stapler and the second handle;
a handle resetting member, positioned between the first handle and the housing of the stapler, and resetting the first handle when an external force is released;
a sliding slot, disposed on the first handle or the second handle, and including a first section and a second section connected with each other;
and a slider, slidably positioned in the sliding slot;
wherein, when the slider is positioned in the first section of the sliding slot, the first handle and the second handle are not linked; when the slider is positioned in the second section of the sliding slot, the first handle and the second handle are linked by the slider.

In some embodiments of the present disclosure, wherein the sliding slot is positioned on the first handle, and the second handle includes a handle abutment; wherein, when the slider is positioned in the first section of the sliding slot and the first handle is rotated in a first direction, the slider is not engaged with the handle abutment, and the second handle remains in an insurance position; when the slider is positioned in the second section of the sliding slot and the first handle is rotated in the first direction, the slider is engaged with the handle abutment to actuate the second handle from the insurance position to a firing position.

In some embodiments, the first handle includes a first cavity having two side walls; two slots are provided in the two side walls, respectively; the slider includes two sliding portions and an abutment in between the two sliding portions, each sliding portion is slidably positioned in a sliding slot.

In some embodiments, a first limit member and a second limit member are provided on each sliding portion and an end of the second section of each slot, respectively; a slider resetting pressure spring is disposed between each first limit member and the corresponding second limit member.

In some embodiments, an outer housing is further provided to the first handle, and a groove is formed at a position of the outer housing corresponding to the sliding slot; the groove includes a first section and a second section corresponding to the first section and second section of the sliding slot; a first limit member and a second limit member are provided at each sliding portion and an end of the second section of each groove, respectively; a slider resetting pressure spring is positioned between each first limit member and the corresponding second limit member.

In some embodiments, a limit portion for the torsion spring is further positioned between the two sliding portions of the slider, and a slider resetting torsion spring is further positioned between the limit portion and the second handle.

In some embodiments, a first end of the first handle includes a gripping portion and a second end of the first handle includes an attachment portion; a first end of the second handle is positioned in a cavity of the attachment portion; when the slider is positioned in the first section of the sliding slot and the first handle is rotated in the first direction, the second handle continues to enter the cavity of the first handle; when the slider is positioned in the second section of the sliding slot and the first handle is rotated in the first direction, the slider prevents the second handle from entering the cavity of the first handle.

In some embodiments, the handle resetting member includes a handle resetting pressure spring which is positioned between the first handle and the housing of the stapler.

In some embodiments, the first pivot pin and the second pivot pin are positioned parallel to each other; a first fixing post and a second fixing post for fixing an end of the second pivot pin are formed on the inner walls of the housings on both sides of the stapler.

In some embodiments, a supporting post is provided, two ends of which are respectively fixed to both sides of the housing of the stapler, and a first end of the torsion spring engages the supporting post, and a second end of the torsion spring engages the inner wall of the second handle.

In some embodiments, a fixing plate is provided between the supporting post and the housing of the stapler; one end of the fixing plate is provided with a curved groove partially wrapping the supporting post, the other end of the fixing plate is fixed to the housing of the stapler;

a first curved portion is further provided on one end of the fixing plate, a holding portion that partially wraps the second torsion spring is provided on a side wall of the fixing plate, a second curved portion is provided on the second end of the first handle, a first end of the second torsion spring engages the first curved portion; and a second end of the second torsion spring is configured to hook the second curved portion.

In some embodiments, the handle resetting member includes a handle resetting pressure spring which is attached to the first handle and the housing of the stapler.

In some embodiments, fixing posts are provided on inner walls on both sides of the housing of the stapler to fix the ends of the pivot pins. A housing fixing portion is provided on the inner walls of the housing of the stapler, a handle fixing portion is provided on the second end of the first handle, and the two ends of the handle resetting pressure spring are fixed to the housing fixing portion and the handle fixing portion respectively.

In some embodiments, a supporting post is provided inside the stapler, two ends of the supporting post are respectively fixed to both sides of the housing of the stapler, and a first end of the torsion spring engages the supporting post, and a second end of the torsion spring engages the inner wall of the second handle;

a fixing plate is positioned between the supporting post and the housing of the stapler, one end of the fixing plate has a curved groove partially wrapping the supporting post, and the other end of the fixing plate is fixed to the housing of the stapler;

the handle resetting pressure spring is positioned in the cavity formed between the fixing plate and the first handle.

In some embodiments, the sliding slot is positioned on the second handle; the first handle includes a handle abutment;

when the slider is positioned in the first section of the sliding slot and the first handle is rotated in a first direction, the handle abutment does not engage the slider, and the second handle remains in an insurance position;

when the slider is positioned in the second section of the sliding slot and the first handle is rotated in the first direction, the handle abutment engages the slider and rotates the second handle from the insurance position to a firing position.

In some embodiments, the position of the slider in the sliding slot is adjusted by an indicator which is movable between a first position area and a second position area; when the indicator moves from the first position area to the second position area, the slider is actuated to move from the first section to the second section of the sliding slot.

In some embodiments, the indicator is attached to a distal end of a pulling sheet, a proximal end of the pulling sheet is sleeved on a screw rod, and a knob is disposed at a distal end of the screw rod; as the knob is rotated, the pulling sheet is moved towards a proximal end of the stapler, thereby moving the indicator from the first position area to the second position area.

In some embodiments, the second handle includes a pulling sheet abutment; when the second handle is rotated from the insurance position to the firing position, the pulling sheet abutment engages the pulling sheet so that a hook of the pulling sheet can be disengaged from the indicator.

The present disclosure further provides a surgical stapler, including any of the aforementioned handle assembly.

The handle assembly and the stapler including the same of present disclosure has the following advantages:

The present disclosure provides a handle assembly and a stapler including the handle assembly. By having a first handle and a second handle, only a movement of the second handle can fire the stapler to perform cutting and suturing operations; during use, an operator can still squeeze the first handle regardless of whether the stapler is ready to be fired. However, when the stapler is not ready to be fired, the movement of the first handle will not engage the second handle, and the stapler cannot be fired; the handle resetting structure design allows the first handle and the second handle to be pivotally attached and rotated around a same rotation center. The rotation center remains unchanged in both the invalid state and the firing state, rendering an enhanced structure stability and improved operator experience.

BRIEF DESCRIPTION OF THE DRAWINGS

Various detailed non-limiting embodiments of the presently disclosure are described herein, with references to the drawings, to elaborate on features, objectives, and advantages.

DETAILED DESCRIPTION

Figure 1:
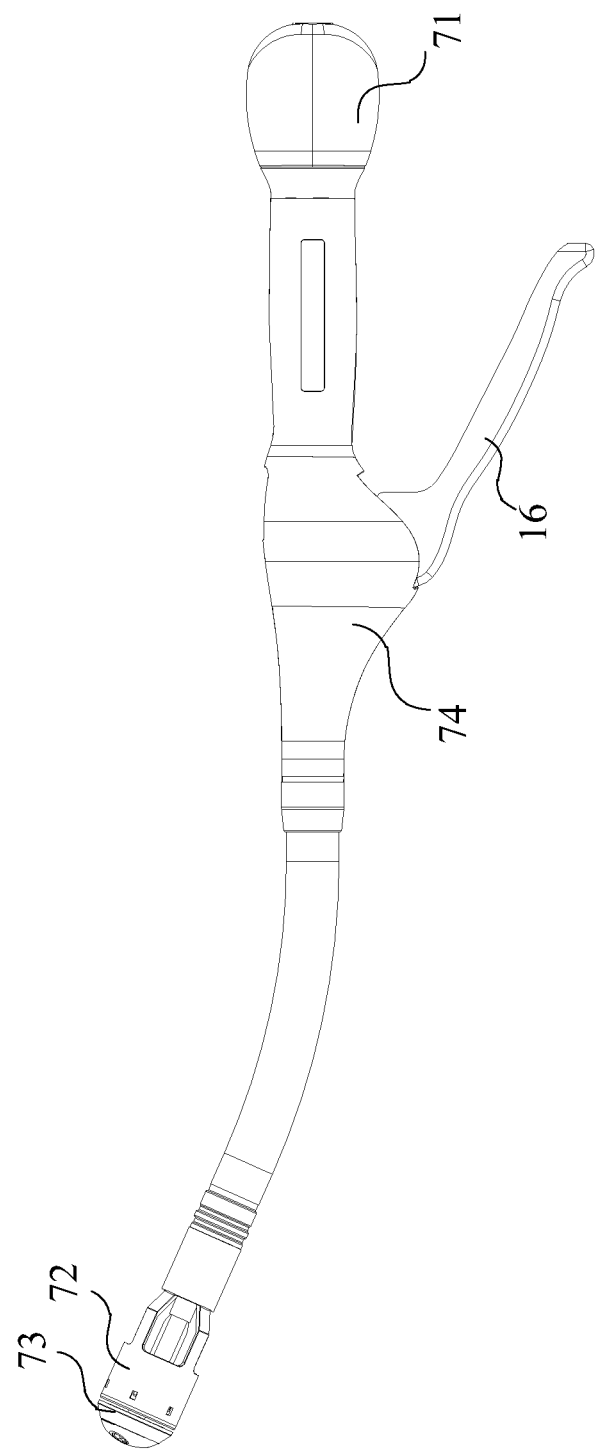
FIG. 1 is a schematic diagram of a stapler according to a first embodiment of the present disclosure.
Figure 2:
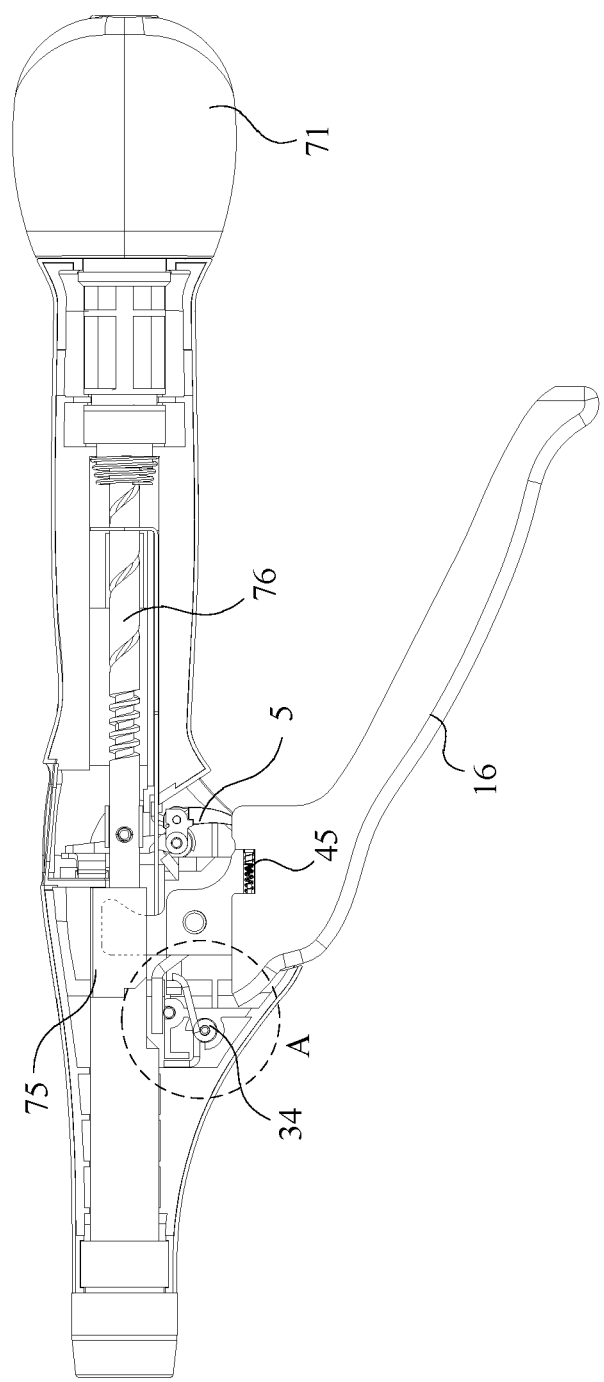
FIG. 2 is a front perspective view according to the first embodiment of the present disclosure when a handle assembly is in an initial position.

In the following, embodiments of the present disclosure will be described in details with reference to the figures. The concept of the present disclosure can be implemented in a plurality of forms, and should not be understood to be limiting. In contrary, these embodiments are provided to make the present disclosure more comprehensible and understandable, and so the conception of the embodiments can be conveyed to those skilled in the art fully. Reference marks in the figures refer to same or similar elements, so repeated description of them will be omitted.

In an effort to tackle the aforementioned technical problems in the prior art, the present disclosure provides a handle assembly for firing a stapler, including: a first handle and a second handle; a first pivot pin, fixedly secured to a housing of the stapler and passing through the first handle and the second handle; a first torsion spring, sleeved on the first pivot, and two ends of the first torsion spring are respectively engaged with the housing of the stapler and the second handle; a handle resetting member, positioned between the first handle and the housing of the stapler, that retracts the first handle when an external force is released; a sliding slot, disposed on the first handle or the second handle, and including a first section and a second section connected with each other; and a slider, slidably positioned in the sliding slot; wherein, when the slider is positioned in the first section of the sliding slot, the first handle and the second handle are not linked; when the slider is positioned in the second section of the sliding slot, the first handle and the second handle are linked by the slider.

Therefore, the present disclosure of the handle assembly provides a first handle and a second handle. Only a movement of the second handle can fire the stapler to perform cutting and suturing operations; during use, an operator can still squeeze the first handle regardless of whether the stapler is ready to be fired. However, when the stapler is not ready to be fired, the movement of the first handle will not engage the second handle, and the stapler will not be fired. The first torsion spring serves as the resetting structure of the second handle, and the handle resetting member serves as the resetting structure of the first handle. When the first handle and the second handle are linked, squeezing the first handle rotates the second handle from the insurance position to the firing position, the first torsion spring and the handle resetting member are deformed, the stapler can be fired. After the stapler has been fired, the first handle is released and reset to the initial position by the handle resetting member, urged by the first torsion spring, the second handle is reset to the insurance position. In addition, when the first handle and the second handle are not linked, squeezing the first handle only rotates the first handle counterclockwise from its initial state and the handle resetting member deforms. When the first handle is released, the first handle is reset to its initial state by the handle resetting member.

The structure of the handle assembly of the present disclosure will be described below in several specific embodiments hereafter, wherein the handle resetting member may be formed of a torsion spring or a pressure spring. Alternatives such as tension springs, elastic metal sheets may be used which all fall within the scope of the present disclosure.

FIGS. 1-21 are schematic views of the stapler according to a first embodiment of the present disclosure. FIG. 1 shows the structure of the stapler of this embodiment. A cartridge assembly 72 and an anvil assembly 73 are provided at the distal end of the stapler, a knob 71 and a handle assembly are provided at the proximal end thereof, and a handle housing 16 is provided on the handle assembly. The stapler can be fired by squeezing the handle assembly.

FIGS. 2-11 show the structure of the handle assembly in an initial position according to an embodiment of the present disclosure. In order to clearly show the structure and mechanism of the handle assembly and the other parts, housing or partial components have been omitted in the figure. The handle assembly according to the present disclosure provides a first handle 1 and a second handle 2. Only when the second handle 2 rotates can the stapler be fired. A first pivot pin 31 passes through both the first handle 1 and the second handle 2. The first pivot pin 31 is fixedly secured to a housing 74 of the stapler, and a first torsion spring 32 is sleeved thereon. Both ends of the first torsion spring 32 are respectively attached to the housing 74 of the stapler and the second handle 2. After rotation, the second handle 2 can be reset as an external force is released.

Since the first handle 1 and the second handle 2 are rotated around a first pivot pin 31, therefore, the first handle 1 and the second handle 2 are unified in the center of rotation thereof, the operator's experience is improved. The center of rotation is unchanged whether the firing was unsuccessful, thus the opening on the housing of handle can be smaller with more appealing appearance, yet rendering a more stable structure of the handle and the stapler.

In this embodiment, the handle resetting member includes a second torsion spring 34 for resetting the first handle 1. In addition, a second pivot pin 33 is provided. The second pivot pin 33 is fixedly secured to the housing 74 of the stapler, the second torsion spring 34 is sleeved on the second pivot pin 33, and two ends of the second torsion spring 34 are respectively attached to the housing 74 of the stapler and the first handle 1.

To realize the linkage of the first handle 1 and the second handle 2, the first handle 1 is further provided with a sliding slot 41 and a slider 42. The sliding slot 41 includes a first section and a second section connected with each other. The second handle 2 includes a handle abutment 25; when the slider 42 is positioned in the first section 411 of the slide slot 41, and the first handle 1 is rotated in the first direction, the slider 42 does not engage the handle abutment 25, the second handle 2 is in an insurance position. Despite that the first handle 1 is rotated, the stapler is in the insurance position, therefore the stapler cannot be fired. In this embodiment, the first direction is the counterclockwise direction shown in the figure, but the present disclosure is not limited to this configuration. Therefore, when an operator squeezes the first handle 1, it can be easily rotated, but the second handle 2 is not triggered. Since the stapler is in an invalid firing state and not fired, the force applied on the first handle 1 is very mall, from which the operator can learn that the stapler has not been fired, and will not cause rupture to the stapler housing.

When the slider 42 is positioned in the second section 412 of the sliding slot 41, and the first handle 1 is rotated in the counterclockwise direction, the slider 42 engages the handle abutment 25 and rotates the second handle 2 from the insurance position to the firing position. When the second handle 2 is rotated in the counterclockwise direction, it simultaneously advances a staple pushing rod 75 distally, thereby firing the stapler.

It should be noted that the first section 411 and the second section 412 of the sliding slot 41 in the present disclosure are relative terms, i.e. not necessarily the two ends of the sliding slot 41. As shown from the perspectives in the figures, the first section 411 of the sliding slot 41 is positioned on the right side of the second section 412. When the slider 42 is positioned in the first section 411 of the slide slot 41, it will not engage the handle abutment 25, whereas positioned in the second section 412 of the slide slot 41, it will engage the handle abutment 25.

In this embodiment, the first handle 1 includes a first cavity 13 having two side walls on both sides, two side walls of the first cavity 13 are respectively provided with a sliding slot 41, and the slider 42 includes two sliding portions 421 and an abutment connecting the two sliding portions 421, each slidably disposed in a sliding slot 41. The handle housing 16 is provided on the outside of the first handle 1, and a groove on the handle housing 16 is also provided at a position corresponding to the sliding slot 41. A first section and a second section of the groove are consistent with the first section 411 and the second section 412 of the sliding slot 41. To limit the movement of the slider 42, the sliding portion 421 is provided with a first limit member 43, and the second section of the groove is provided with a second limit member. A slider resetting pressure spring is disposed between the first limit member and the corresponding second limit member.

The movement of the slider 42 from the first section 411 to the second section 412 of the sliding slot 41 is adjusted by the indicator 5. The indicator 5 includes a first end 51, a positioning portion 53 and a second end 52. The first end 51 of the indicator 5 is provided with a protrusion 54 which corresponds to the position of a hook 61 of a pulling sheet 6. The positioning portion 53 of the indicator 5 is pivotally attached to the housing 74 of the stapler. The tail 62 of the pulling sheet 6 is fixed to a screw rod 76 and will move along the screw rod 76. When the knob 71 is rotated in one direction, the screw rod 76 will move towards the proximal end of the stapler, moving the pulling sheet 6 proximally. The hook of the pulling sheet 61 may then effect a movement of the first end 51 of the indicator 5 in the second direction, so that when the first end 51 of the indicator 5 moves from the first position area to the second position area, the second end 52 of the indicator 5 further moves the slider 42 from the first section 411 to the second section 412 of the sliding slot 41. In this embodiment, the second direction is the clockwise direction shown in the figure, but the present disclosure is not limited to this configuration. A window is provided on the stapler body portion corresponding to the first position area and the second position area, for the purpose of observing the position of the first end 51 of the indicator during use. When the first end 51 of the indicator is in the first position area, the stapler cannot be fired. When the first end 51 of the indicator is in the second position area, the stapler can be fired. In order to cue the operator that the stapler is in firing position, the second position area is marked in green, which has been disclosed in the prior art.

Figure 3:
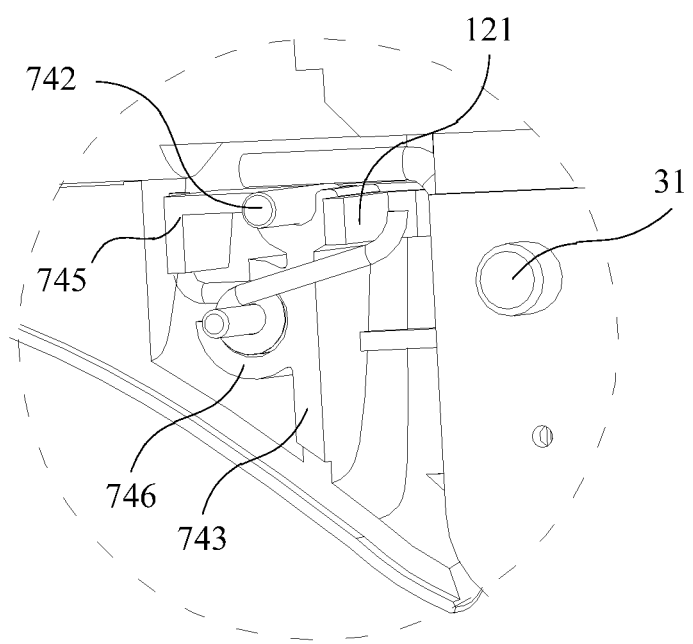
FIG. 3 is a perspective view from A in FIG. 2.
Figure 4:
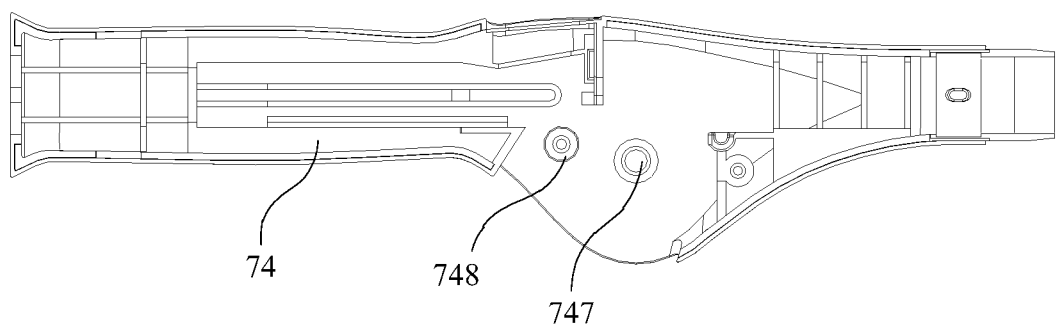
FIG. 4 is a schematic view of an inner side wall of a stapler housing according to the first embodiment of the present disclosure.

In this embodiment, FIGS. 3 and 4 show the configuration of the first pivot pin 31 and the second pivot pin 33. The first pivot pin 31 and the second pivot pin 33 are positioned parallel to each other, and the inner walls of the housing 74 on both sides of the stapler are provided with a first fixing post 747 and a second fixing posts 748, respectively, for fixedly securing the ends of the first pivot pin 31 and the second pivot pin 33. Both ends of the first pivot pin 31 are inserted into the first fixing post 747, and both ends of the second pivot pin 33 are inserted into the second fixing post 748. A supporting post 742 is provided inside the stapler to limit the position of the first end of the first torsion spring 32 on the housing. The supporting post 742 is parallel to the first pivot pin 31. Two ends of the supporting post 742 are fixedly secured to both sides of the housing 74 of the stapler. The first end of the first torsion spring 32 is attached to the supporting post 742 and the second end to the inner wall of the second handle 2. As shown in the figures, the second end of the first torsion spring 32 abuts the inner wall of the handle abutment 25. A fixing plate 743 is provided between the supporting post 742 and the housing of the stapler to support and locate the supporting post 742. One end of the fixing plate 743 is provided with a curved groove 744 partially wrapping the supporting post 742. The other end of the fixing plate 743 is fixed to the housing 74 of the stapler to strengthen the housing; one end of the fixing plate 743 is also provided with a first curved portion 745, a side of the fixing plate 743 is provided with a torsion spring holding portion 746 that partially wraps the second torsion spring 34, the second end of the first handle 1 is provided with a second curved portion 121, the first end of the second torsion spring 34 engages the first curved portion 745, and the second end of the second torsion spring 34 is configured to hook the second curve portion 121.

Figure 5:
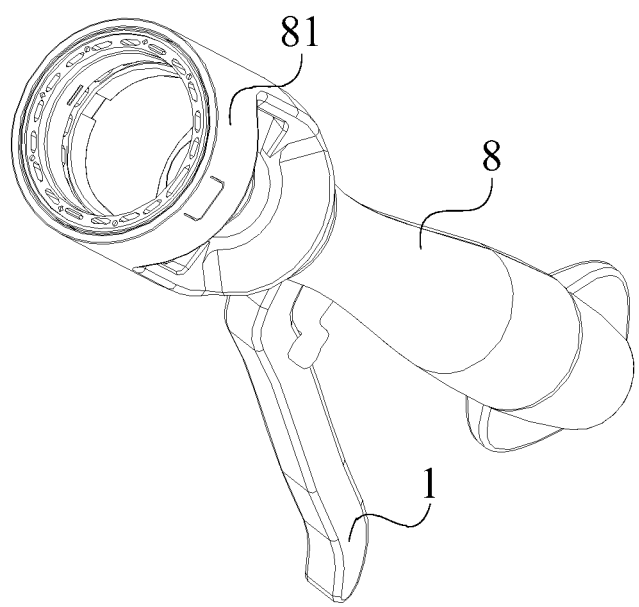
FIG. 5 is a schematic view of the handle assembly according to the first embodiment of the present disclosure applied in a circumcision stapler.
Figure 6:
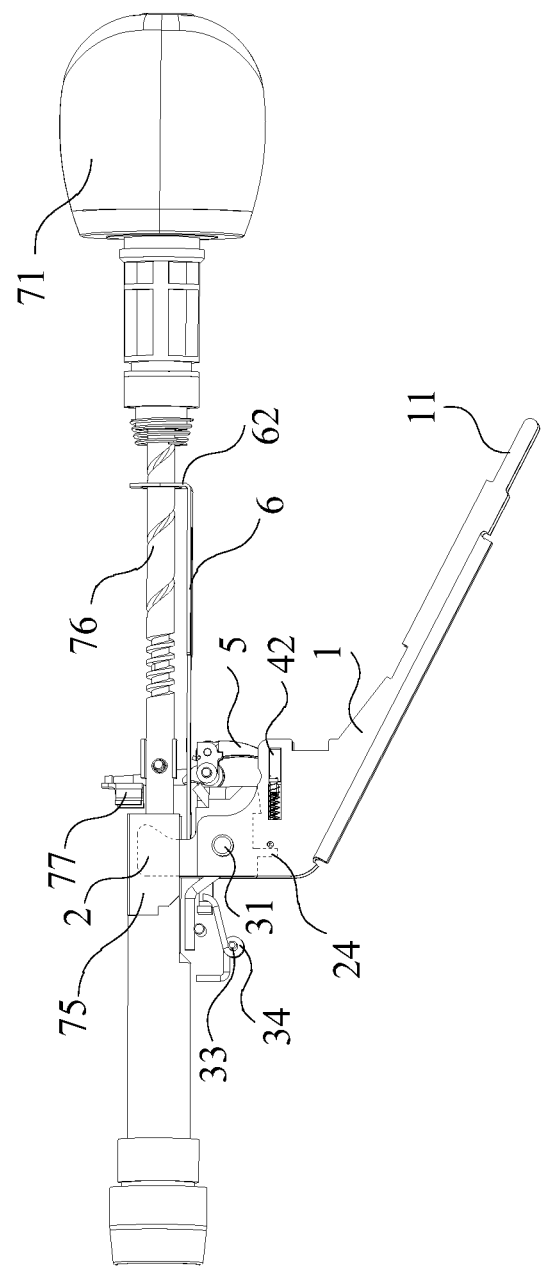
FIG. 6 is a schematic view of the handle assembly according to the first embodiment of the present disclosure in an initial position.
Figure 7:
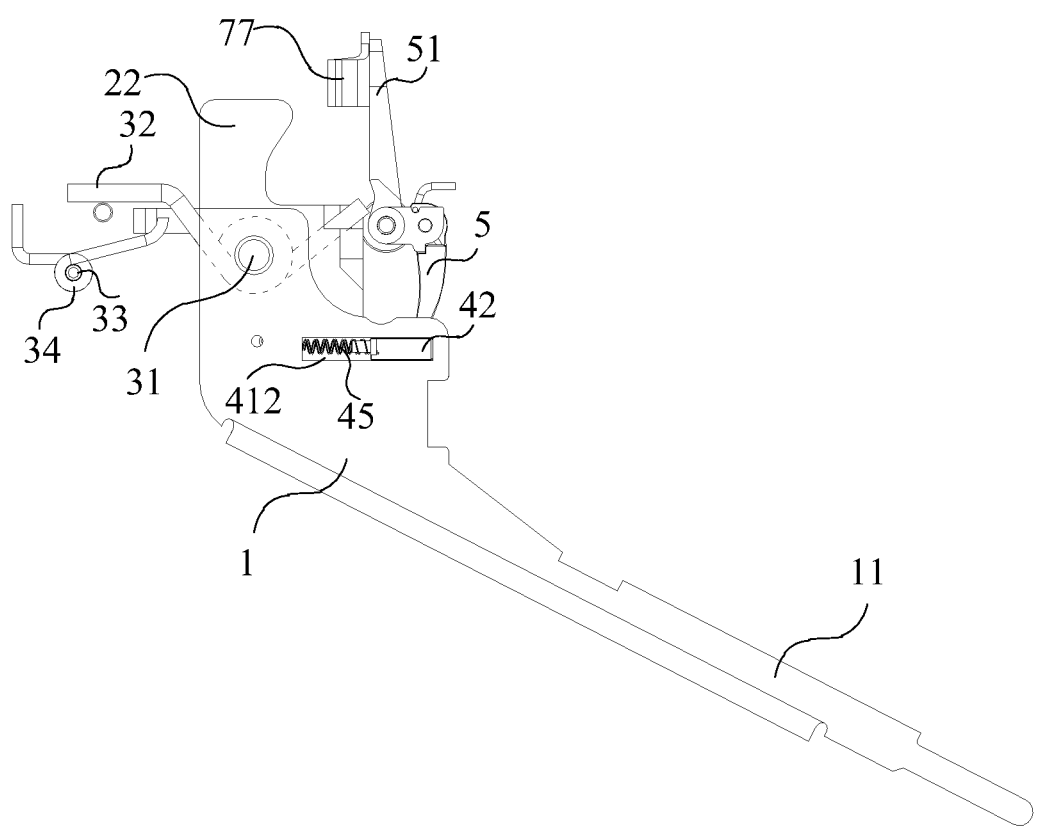
FIG. 7 is a schematic view of the handle assembly according to the first embodiment of the present disclosure in an initial position.
Figure 8:
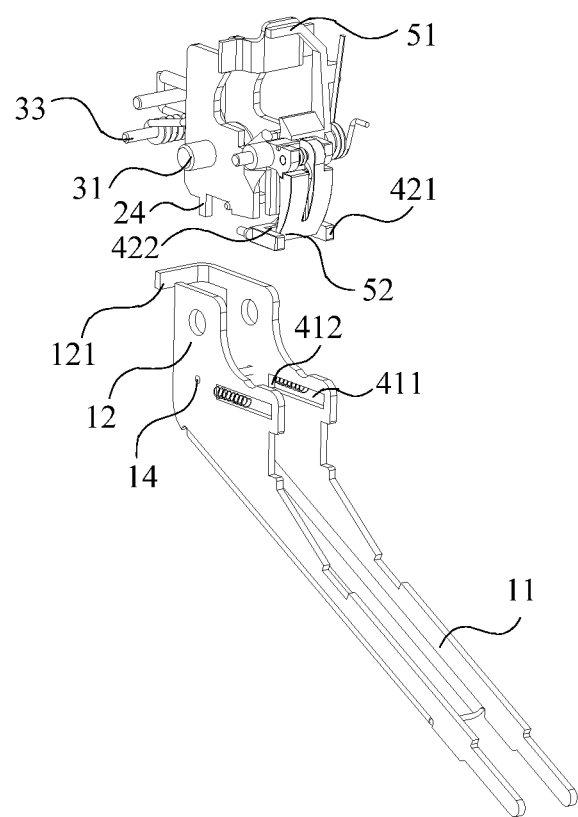
FIG. 8 is an exploded view of the handle assembly in the initial position according to the first embodiment of the present disclosure.
Figure 9:
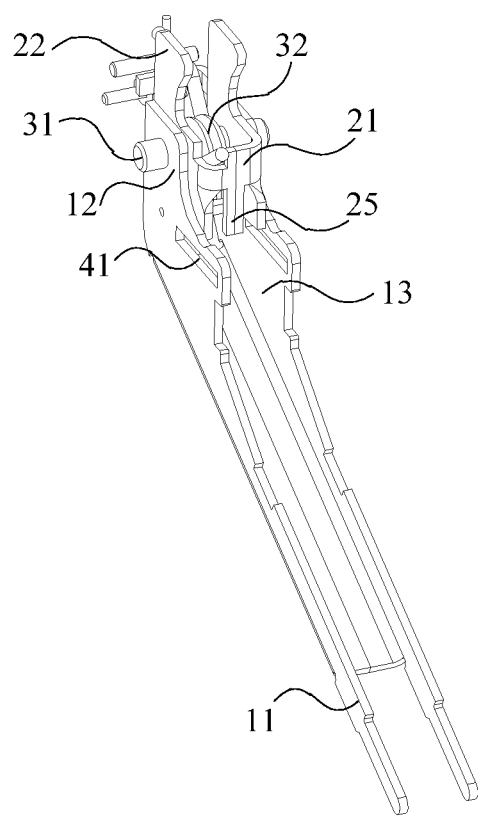
FIG. 9 is a schematic view of the interconnection between the first handle and the second handle according to the first embodiment of the present disclosure.
Figure 10:
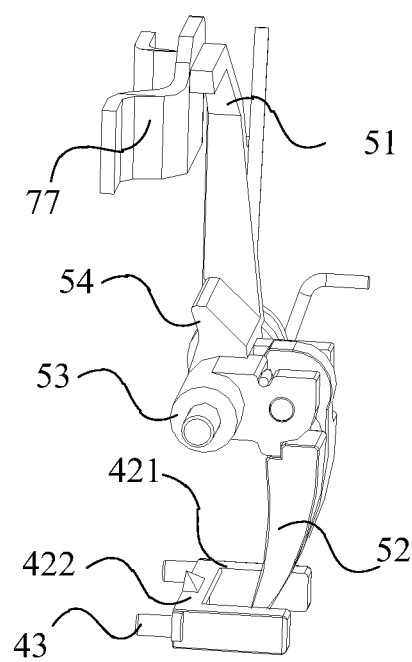
FIG. 10 is a schematic view of the slider and the indicator in FIG. 2.
Figure 11:
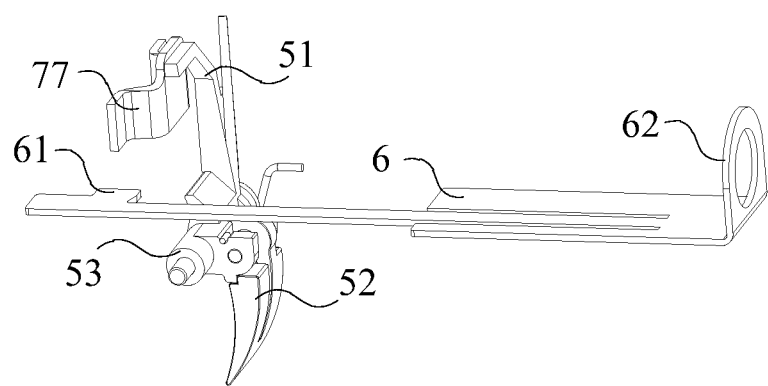
FIG. 11 is a schematic view of the interconnection between the pulling sheet and indicator in FIG. 2.
Figure 12:
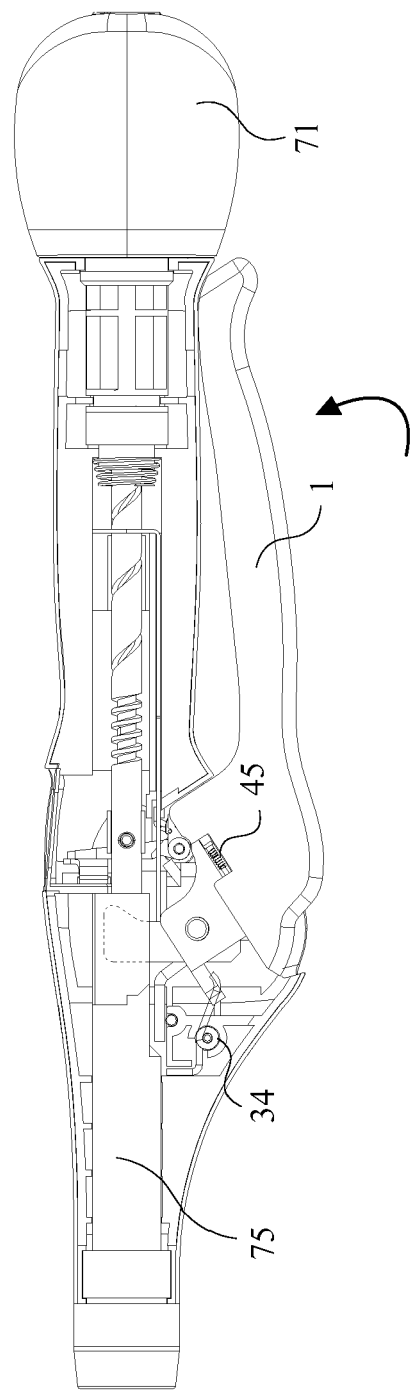
FIG. 12 is a schematic view of the handle assembly in an invalid state according to the first embodiment of the present disclosure.

The present disclosure can be applied not only to a conventional circular stapler, but also to a circumcision stapler. For example, FIG. 5 shows the structure of a body portion 8 of the circumcision stapler. The distal end of the circumcision stapler body portion 8 includes a cartridge assembly 81, and a glans cap assembly (not shown in the figure) that corresponds to the cartridge assembly 81. In using a circumcision stapler, the second handle 2 is movably connected to one end of the circumcision stapler. The second end of the second handle 2 is configured to urge the staple pushing rod when the firing condition is met in order to fire the circumcision stapler.

FIGS. 12 to 16 show the structure of the handle assembly of the same embodiment when in an invalid state. In this state, the pulling sheet 6 cannot pull the indicator 5, so the position of the first section 51 of the indicator 5 is unchanged in the first position area. The slider 42 is still positioned in the first section 411 of the slide slot 41. In its rotational path, the slider 42 does not engage the handle abutment 25 of the second handle 2. It should be noted that, in the initial state, the slider 42 is positioned by the slider resetting pressure spring 45 at the right end of the first section of the sliding slot 41 and far from the second section, which is to the right of the drawing. Alternatively, the initial position of the slider 42 may be limited by a second end 52 of the indicator 5. In this embodiment, a first end 11 of the first handle 1 is a gripping portion, and a second end 12 includes an attachment portion; a first end 21 of the second handle 2 is positioned inside the cavity of the attachment portion, and a second end 22 engages the staple pushing rod 75. As such, the stapler is in an insurance state. Since the torsion force of the second torsion spring 34 is much smaller compared to the force required for firing the stapler, the first handle 1 can be rotated counterclockwise around the first pivot pin 31 with a very small force, and the second handle 2 continues to enter inside the cavity of the first handle 1. As the first handle 1 and the second handle 2 are not linked, when the first handle 1 is forced to rotate, it does not rotate the second handle 2 thus the firing of the stapler cannot be completed. The stapler provides a tactile feedback that the first end 51 of the current indicator 5 has not reached the second position area and the stapler has not been fired. When the external force is released, the first handle 1 is reset by the second torsion spring 34.

FIGS. 17 to 21 show the structure of the handle assembly of the same embodiment when the stapler is in a firing position. In this position, turning the knob 71 causes the screw rod 76 to effect advancement of the pulling sheet 6 proximally, and rotates the first end 51 of the indicator 5 clockwise to move from the first position area to the second position area. The second end 52 of the indicator 5 pushes the slider 42 toward the second section 412 of the slide slot 41 to engage the handle abutment 25. When the first handle 1 is squeezed and rotated counterclockwise, the slider 42 engages the handle abutment 25 and prevents the second handle 2 from continuing to enter the internal cavity of the first handle 1. As such, the second handle 2 and the first handle 1 become linked. The second handle 2 is rotated counterclockwise in synchronization with the first handle 1, and the second end 22 of the second handle 2 pushes the staple pushing rod 75 which further pushes a pusher sheet and a circular cutter of the stapler in performing suturing and cutting operations.

As shown in FIGS. 17 to 21, the slider resetting pressure spring 45 is further compressed during the movement of the slider 42. The second handle 2 is further provided with a pulling sheet abutment 23. When the second handle 2 is rotated from the insurance position to the firing position, the pulling sheet 6 is ejected by the pulling sheet abutment 23 at an ejection point 231, so that the hook 61 of the pulling sheet 6 is separated from the indicator 5. Actuated by the resetting spring, the indicator 5 will automatically return to the initial position. With a single rotation center structure of this embodiment, the pulling sheet abutment 23 is closer to a contacting point of the pulling sheet, the pulling sheet 6 is more easily ejected and the indicator less likely to be stuck due to failed ejection. Since the first end 51 of the indicator 5 returns to the first position area, the second end 52 of the indicator 5 is separated from the slider 42. No longer being pushed by the indicator 5, the slider 42 will be biased to the first section 411 of the sliding slot 41 under the resetting force of the slider resetting pressure spring 45 before the reset is complete. After the stapler is fired, the first handle 1 is released, and the second handle 2 is reset by the resetting force of the first torsion spring 31; as the first handle 1 is engaged with the second handle 2 due to the slider, the first handle 1 is firstly reset along with the second handle 2, and then reset by the second torsion spring 34.

Further, in this embodiment, a metal sheet 77 is provided in the housing 74 of the stapler at a position corresponding to the first end 51 of the indicator 5, and when the indicator 5 returns to its initial position, it will engage the metal sheet 77, making a clicking sound cueing the operator that the indicator 5 has been reset.

Figure 13:
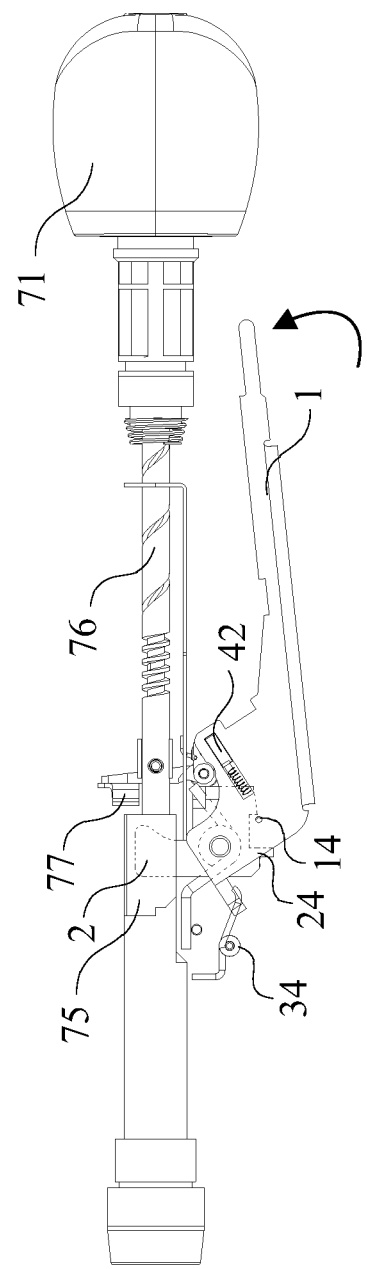
FIG. 13 is a schematic view of the handle assembly in an invalid state according to the first embodiment of the present disclosure.
Figure 14:
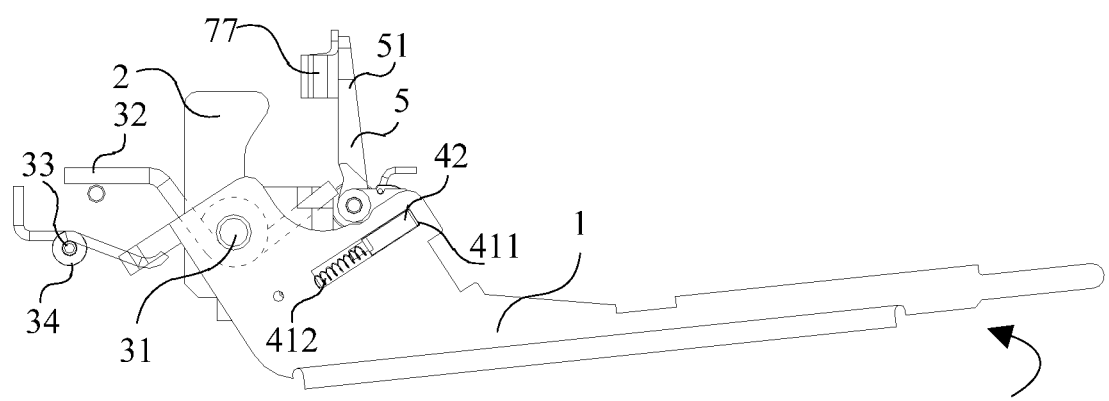
FIG. 14 is a schematic view of the handle assembly in an invalid state according to the first embodiment of the present disclosure.
Figure 15:
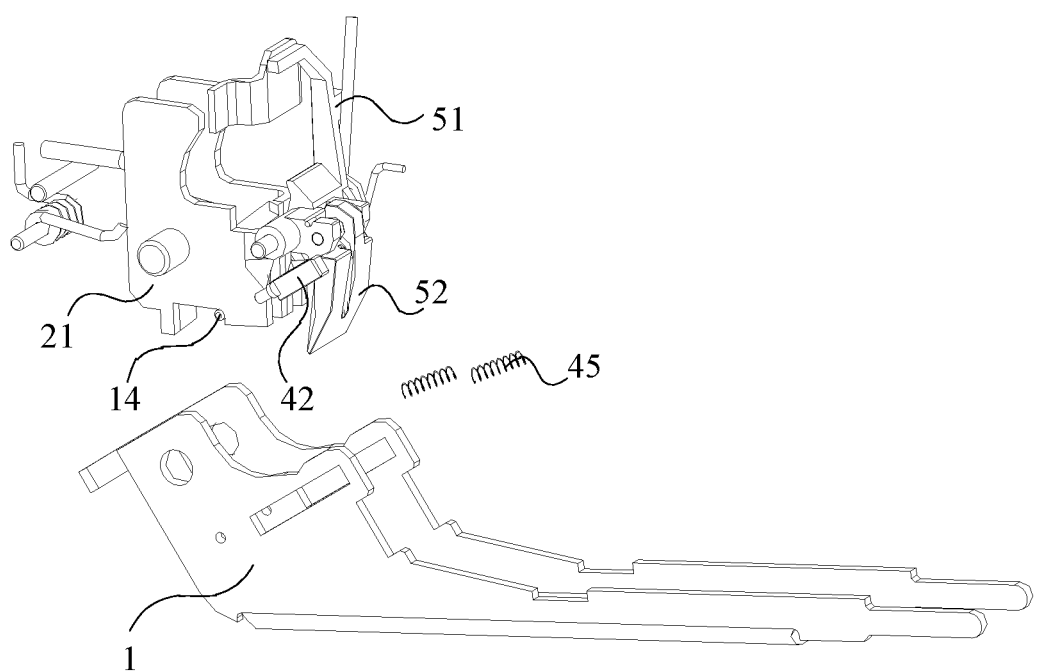
FIG. 15 is an exploded view of the handle assembly in the invalid state according to the first embodiment of the present disclosure.
Figure 16:
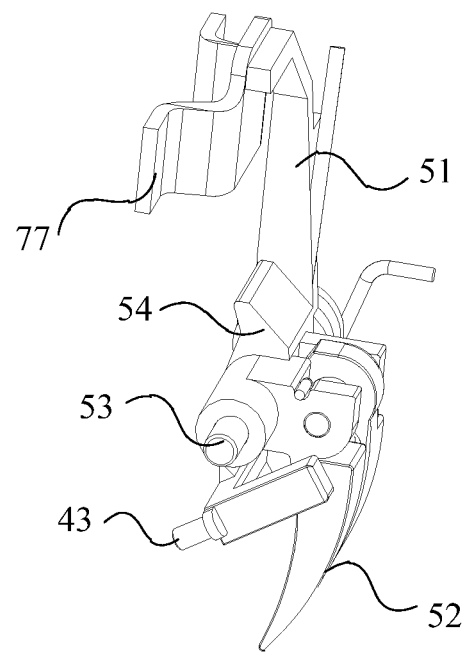
FIG. 16 is a schematic view of the slider and the indicator in FIG. 12.
Figure 17:
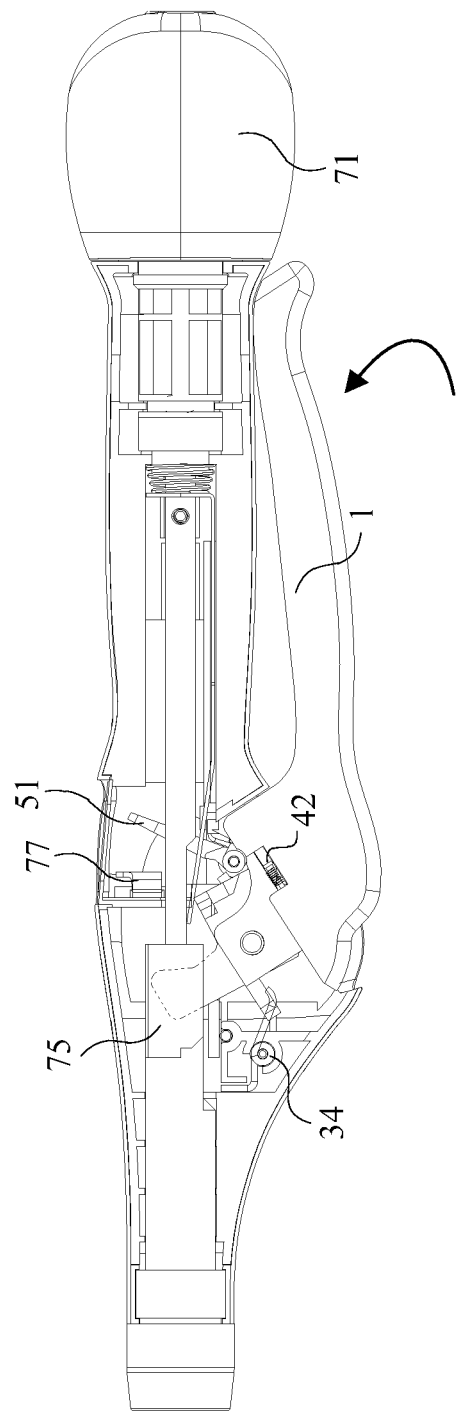
FIG. 17 is a schematic view of the handle assembly in a firing position according to the first embodiment of the present disclosure.
Figure 18:
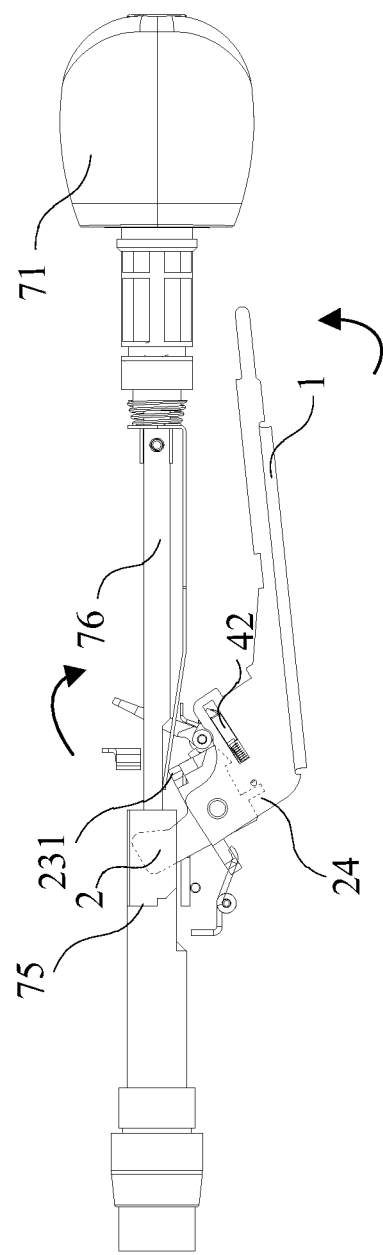
FIG. 18 is a schematic view of the handle assembly in a firing position according to the first embodiment of the present disclosure.
Figure 19:
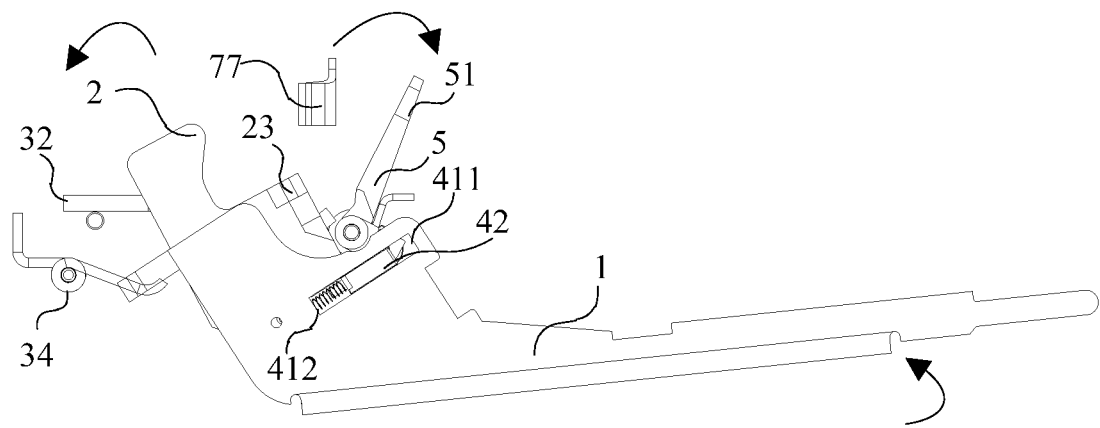
FIG. 19 is a schematic view of the handle assembly in a firing position according to the first embodiment of the present disclosure.
Figure 20:
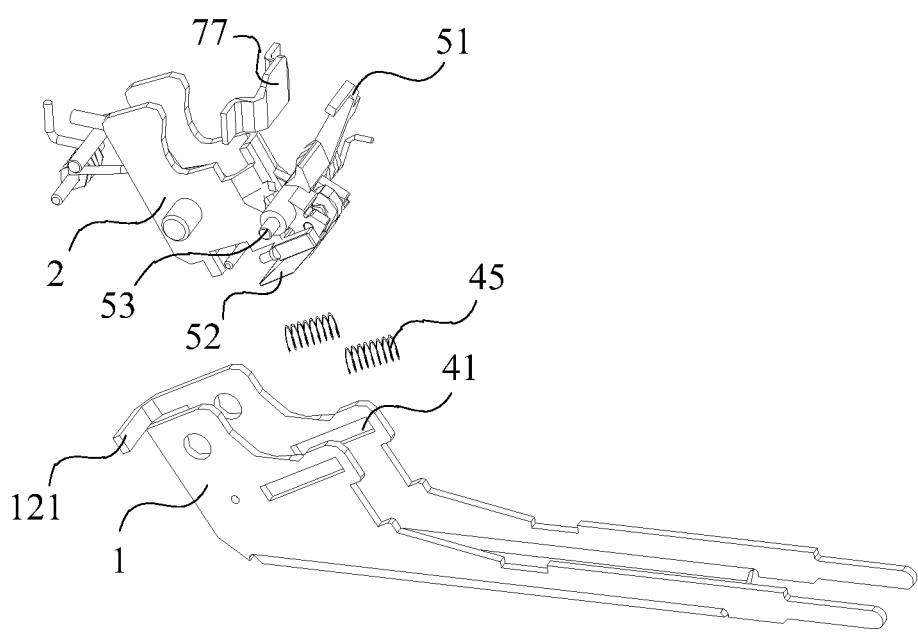
FIG. 20 is an exploded view of the handle assembly in a firing position according to the first embodiment of the present disclosure.
Figure 21:
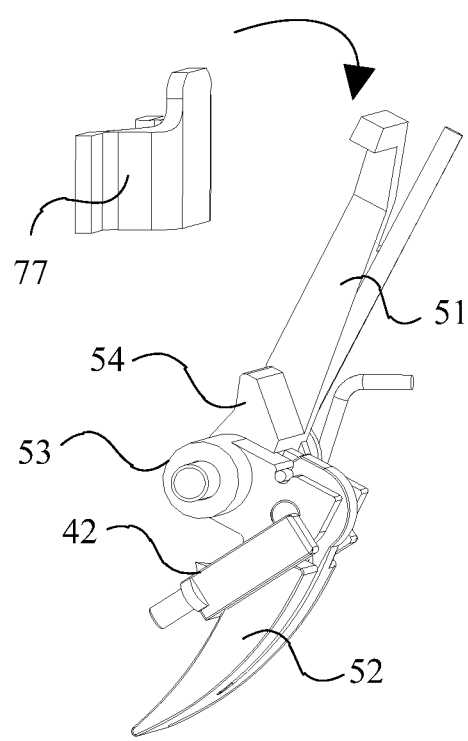
FIG. 21 is a schematic view of the slider and the indicator in FIG. 17.

As shown in FIG. 13, furthermore, in this embodiment, in order to limit the position of the first handle 1 in the initial position and prevent the opening angle of the first handle 1 from being too large, a stop pivot pin 14 is provided inside the cavity of the second end 12 of the first handle 1. The first end 21 of the second handle 2 are provided with a second handle limit portion 24; when the first handle 1 is not rotated under pressure, the stop pivot pin 14 abuts the handle limit portion 24 to prevent the first handle 1 from rotating clockwise as shown in the figure, precisely locating the first handle 1 at its initial position. However, the stop pivot pin 14 and the second handle limit portion 24 have no effect on the counterclockwise rotation of the first handle 1, and therefore will not affect the normal operation of the handle assembly. Moreover, with this configuration, the initial position of the second handle 2 can also be limited.

FIGS. 22 to 26 show schematic views of a handle assembly according to a second embodiment of the present disclosure. Its difference from the first embodiment is that the handle resetting member includes a handle resetting pressure spring 35 used for resetting the first handle 1. Two ends thereof are respectively attached to the first handle 1 and the housing 74 of the stapler. Specifically, a handle fixing portion 352 may be provided on the first handle 1, a housing fixing portion 351 may be provided on the housing 74 of the stapler, and both ends of the handle resetting pressure spring 35 are respectively fixedly secured to the handle fixing portion 352 and the housing fixing portion 351. When the first handle 1 is in its initial position, the handle resetting pressure spring 35 is not deformed. However, when the first handle 1 is rotated counterclockwise by an external force, it will squeeze and deform the handle resetting pressure spring 35. When the external force is released, the handle resetting pressure spring 35 biases the first handle 1 to the initial position. Only one handle resetting pressure spring 35 is shown in the figure. In practical applications, the number and type of pressure springs can be tailored to the actual requirements, and all configurations fall within the scope of the present disclosure.

Figure 22:
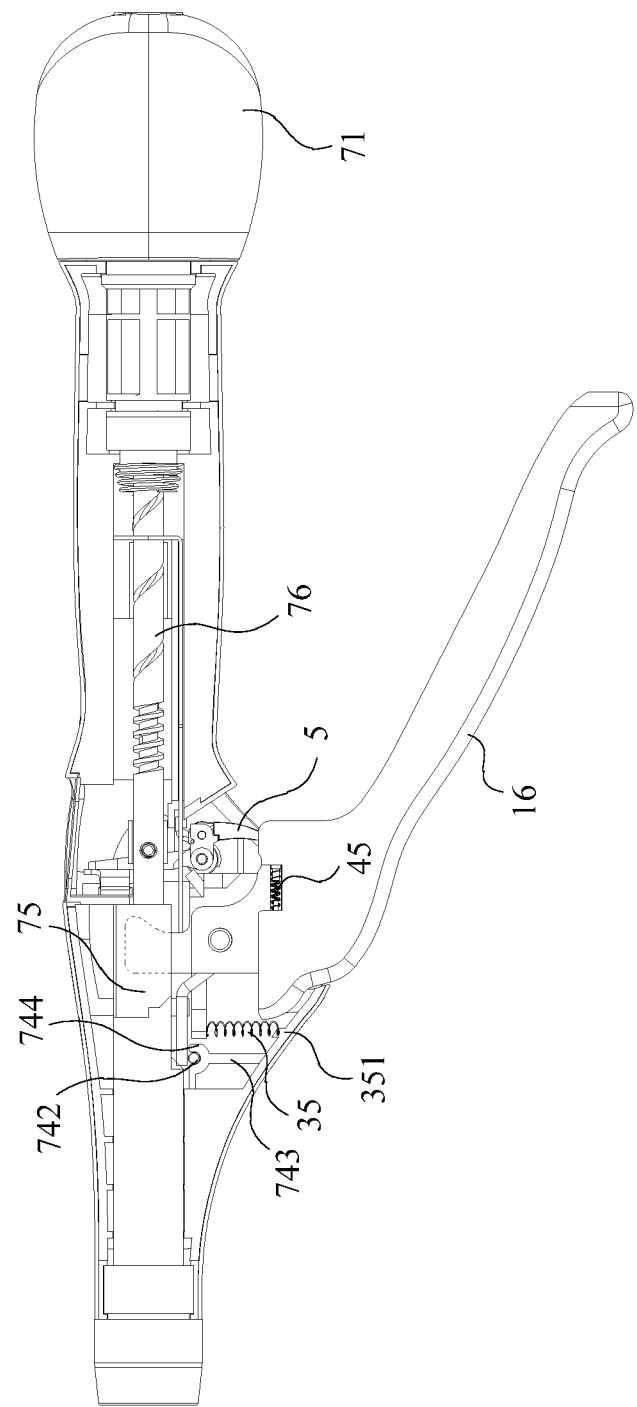
FIG. 22 is a schematic view of the handle assembly according to a second embodiment of the present disclosure applied in a conventional circular stapler.
Figure 23:
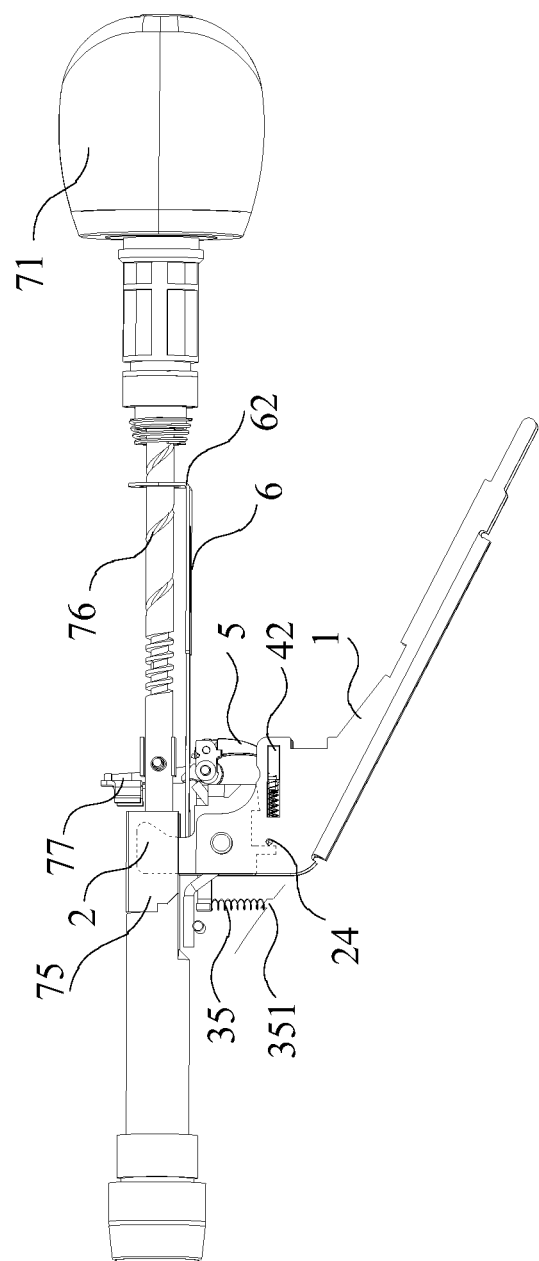
FIG. 23 is a schematic view of the handle assembly in the initial position according to the second embodiment of the present disclosure.

For the specific setting of the handle resetting pressure spring 35, refer to the structures shown in FIG. 22 and FIG. 23. A supporting post 742 is provided inside the stapler for restricting the position on the housing of the first end of the first torsion spring 32. The two ends of the supporting post 742 are fixed to both sides of the housing 74 of the stapler respectively. The first end of the spring 32 abuts the supporting post 742, and the second end of the first torsion spring 32 abuts the inner wall of the second handle 2; a fixing plate 743 is provided between the supporting post 742 and the housing 74 of the stapler. One end of the fixing plate 743 is provided with a curved groove 744 that partially wraps the supporting post, and the other end of the fixing plate 743 is fixed to the housing 74 of the stapler to strengthen the housing; the handle resetting pressure spring 35 is positioned in the cavity formed between the first handle and the fixing plate 743. Such structural layout fully utilizes the internal cavity, stabilizes each member component, and offers a more compact overall structure.

Figure 24:
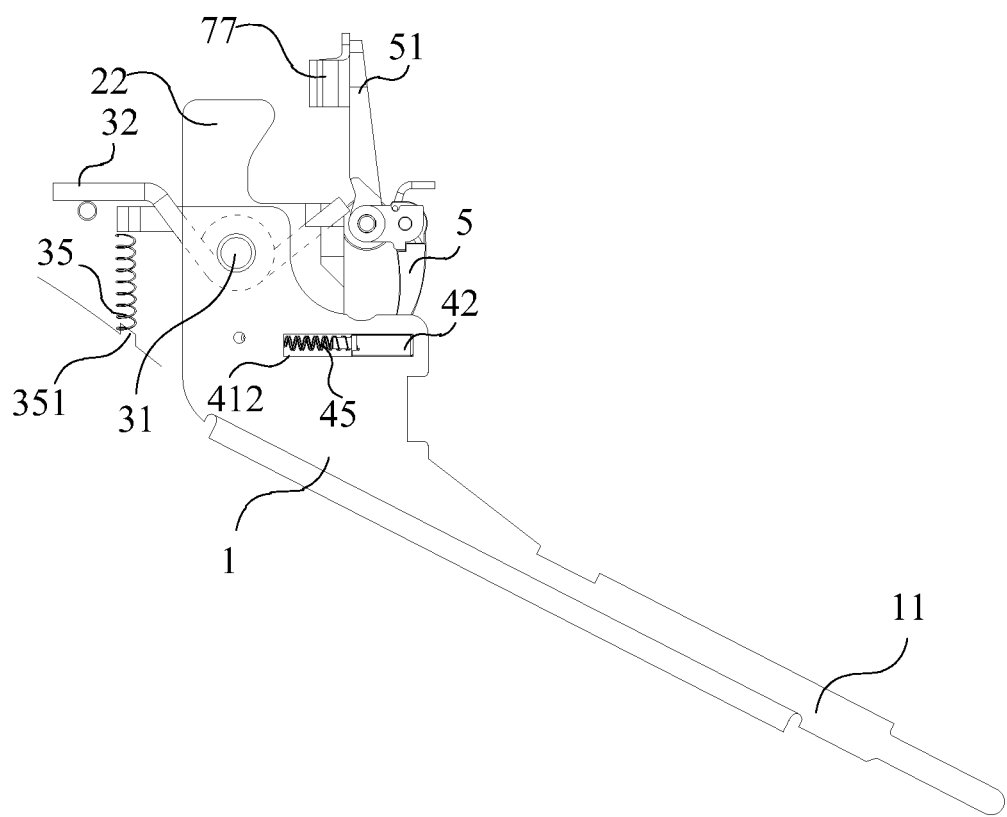
FIG. 24 is a schematic view of the handle assembly in the initial position according to the second embodiment of the present disclosure.

FIG. 24 is a schematic view of the handle assembly according to this embodiment when the handle assembly is in the initial state, wherein neither the first handle 1 nor the second handle 2 is rotated. Neither the handle resetting pressure spring 35 nor the first torsion spring 32 is deformed.

Figure 25:
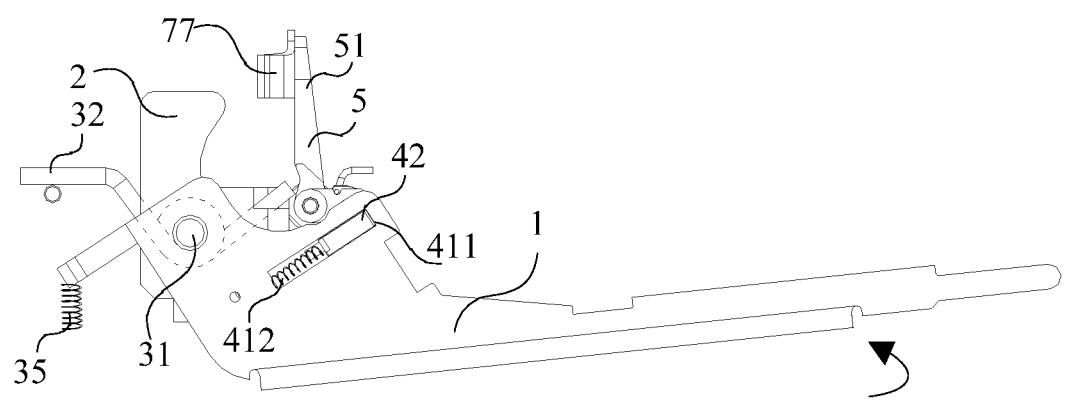
FIG. 25 is a schematic view of the handle assembly in the invalid state according to the second embodiment of the present disclosure.

FIG. 25 is a schematic view of the handle assembly according to this embodiment when the handle assembly is in an invalid state, wherein the position of the indicator 5 remains in the first position area due to lacking a pulling force of the pulling sheet 6. The slider 42 is still positioned in the first section 411 of the sliding slot 41. On the rotation path of the first handle 1, the slider 42 does not engage the handle abutment 25 of the second handle 2. As such, the stapler is in the insurance state. Since the compressive force of the handle resetting pressure spring 35 is much smaller than the firing force, the first handle 1 can rotate counterclockwise around the pivot pin 31 with less force, and the second handle 2 continues to enter inside the cavity of the first handle 1. The first handle 1 and the second handle 2 are not linked. As such the second handle 2 is not rotated and the stapler is not fired. The stapler returns a tactile feedback that the first end 51 of the current indicator 5 has not reached the second position area and the stapler has not been fired. When the external force is released, the first handle 1 is biased and reset by the second torsion spring 35.

Figure 26:
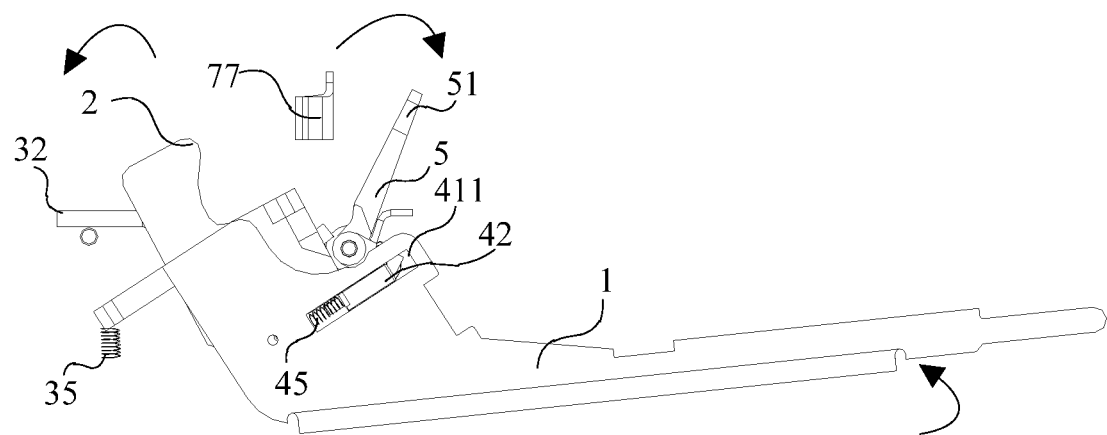
FIG. 26 is a schematic view of the handle assembly in the firing position according to the second embodiment of the present disclosure.

FIG. 26 is a schematic view of the handle assembly according to this embodiment when the handle assembly is in a firing position, wherein rotating the knob 71 causes the screw rod 76 to move the pulling sheet 6 proximally, and drives the first end 51 of the indicator 5 to move clockwise, so that the first end 51 of the indicator 5 enters the second position area from the first position area. The second end 52 of the indicator 5 pushes the slider 42 to move toward the second section 412 of the sliding slot 41 to engage the handle abutment 25. When the first handle 1 is squeezed, the slider 42 engages the handle abutment 25 and prevents the second handle 2 from continuing to enter the internal cavity of the first handle 1. As a result, the second handle 2 and the first handle 1 become linked. The second handle 2 is rotated counterclockwise with the first handle 1. The second end of the second handle 2 pushes the staple pushing rod 75 which further pushes the pusher sheet and circular cutter of the stapler in performing the operations. Both the first torsion spring 32 and the handle resetting pressure spring 35 are deformed. Therefore, after the stapler is fired and the external force is released, the first handle 1 and the second handle 2 are reset under the resetting force of the torsion spring 31. As the first handle 1 is engaged with the second handle 2 due to the slider, the first handle 1 is firstly reset along with the second handle 2 and then reset by the second torsion spring 35.

Figure 27:
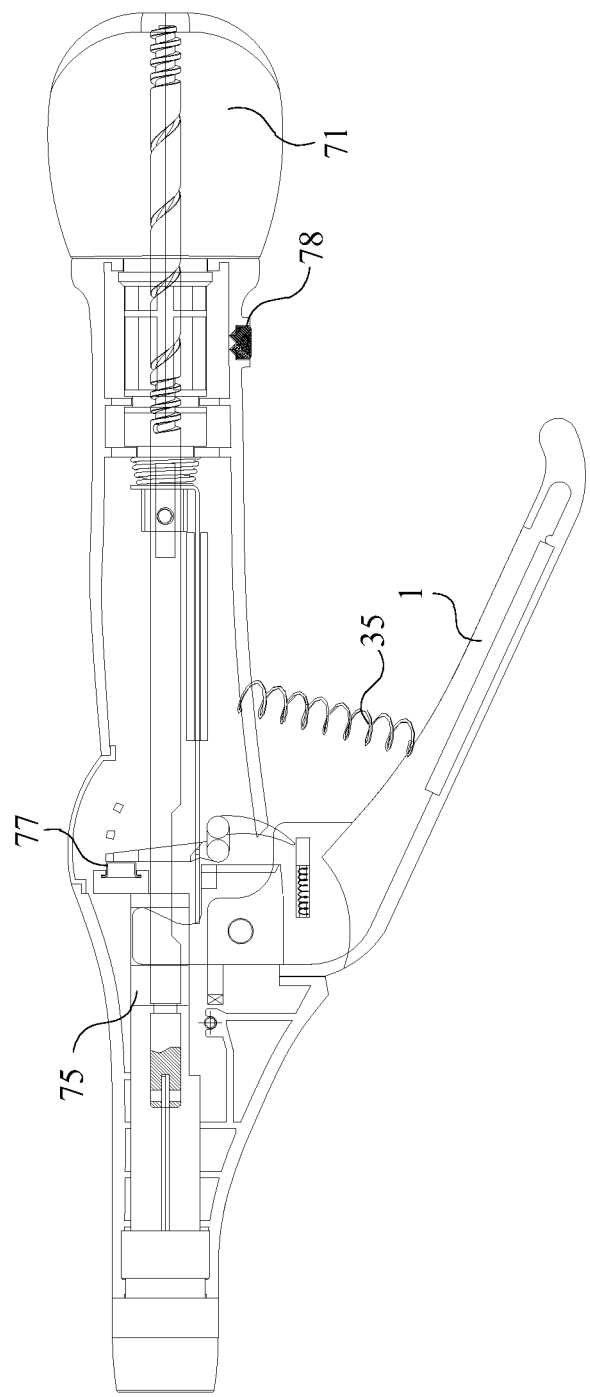
FIG. 27 is a schematic view of the handle assembly applied to a circular stapler according to a third embodiment of the present disclosure.

FIG. 27 is a schematic view of a handle assembly according to a third embodiment of the present disclosure. It differs from the second embodiment in that the handle resetting pressure spring 35 is provided on the other side of the first handle 1. Similarly, the handle resetting pressure spring 35 is compressed as the first handle 1 is squeezed and biased to retract as the first handle 1 is released. In this embodiment, the handle resetting pressure spring 35 may be disposed between the first handle 1 itself and the housing 74 of the stapler, or may be disposed between the handle housing 16 and the housing 74 of the stapler. The insurance state, firing state and reset process of the stapler in this embodiment are similar to the second embodiment, and will not be repeatedly described here.

Figure 28:
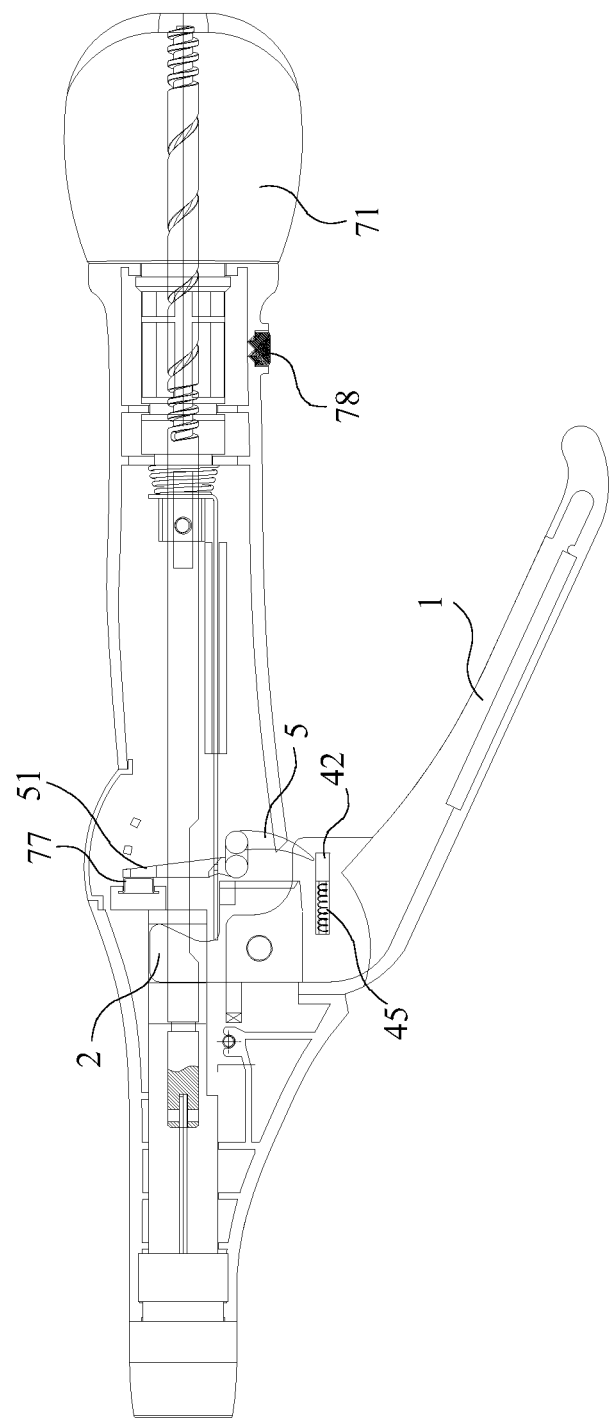
FIG. 28 is a schematic view of the handle assembly in the initial position according to a fourth embodiment of the present disclosure.
Figure 29:
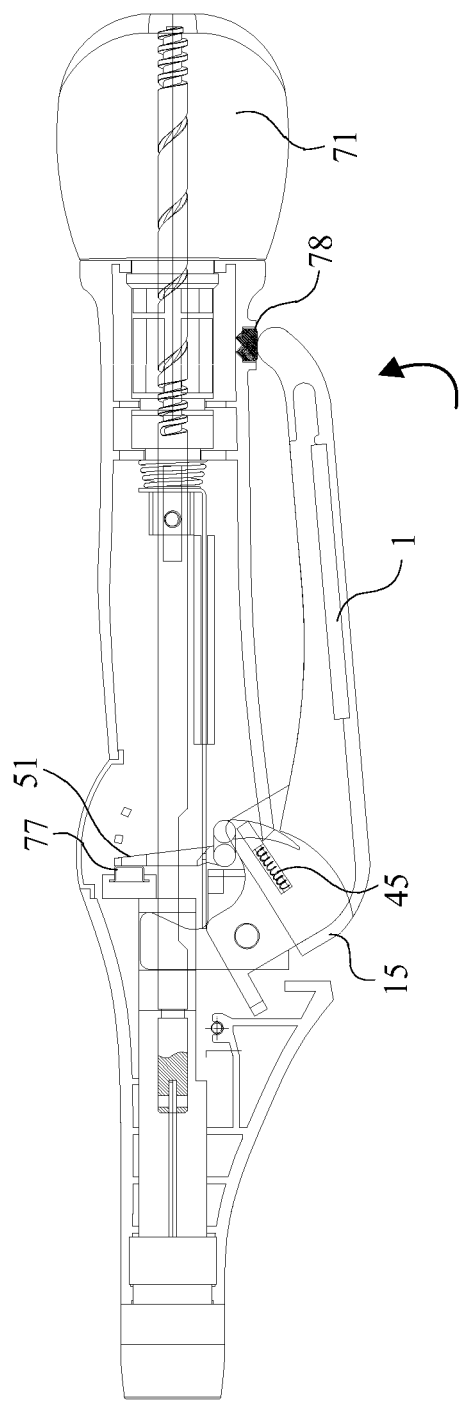
FIG. 29 is a schematic view of the handle assembly in the invalid state according to the fourth embodiment of the present disclosure.
Figure 30:
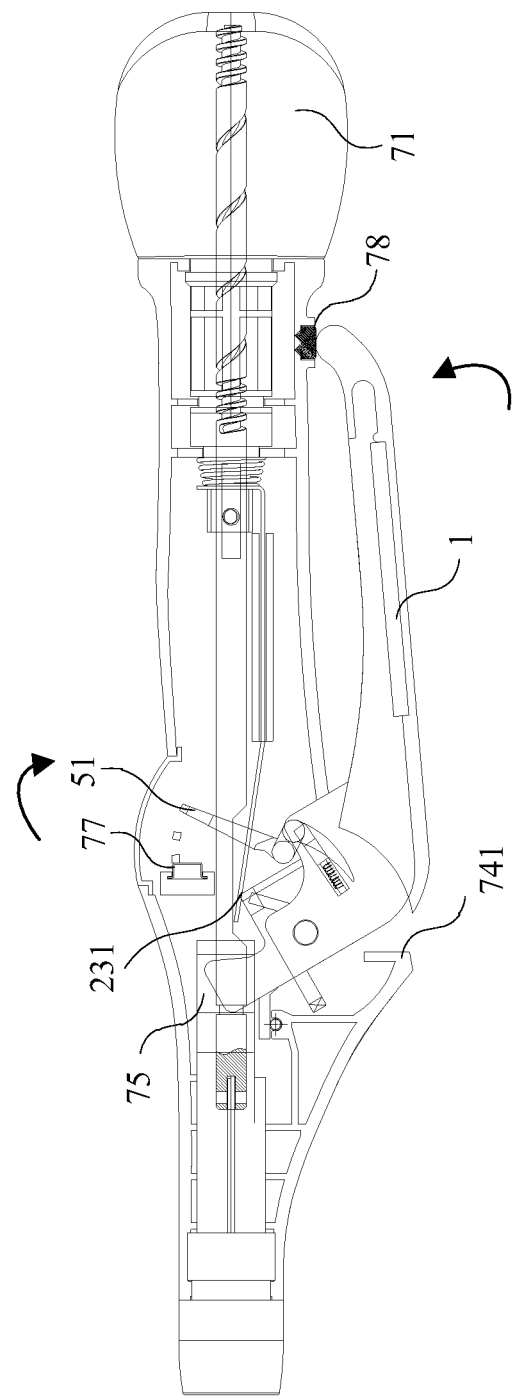
FIG. 30 is a schematic view of the handle assembly in the firing position according to the fourth embodiment of the present disclosure.

FIGS. 28-30 are schematic views of a handle assembly according to a fourth embodiment of the present disclosure. In this embodiment, the technical design differs from the previous three embodiments in that: a second stop structure that limits the slider resetting pressure spring 45 is directly provided at the end of the second section 412 of the sliding slot 41. In addition, in this embodiment, the first handle 1 and the stapler housing 74 are provided with a first handle abutment 15, and the stapler housing 74 is provided with a housing abutment 741; when the first handle 1 is not rotated under pressure, the first handle limit portion 15 abuts on the housing limit portion 741 to prevent the first handle 1 from rotating clockwise.

As shown in FIG. 28, the handle assembly is in an initial position where the indicator 5 is in the first position area and not rotated by the pulling sheet 6, and the slider 42 is positioned in the first section 411 of the slide slot 41. As shown in FIG. 29, the handle assembly is in the invalid state; the second handle 2 continues to enter the cavity of the first handle 1. The two handles are not linked thus squeezing the first handle 1 does not fire the stapler. As shown in FIG. 30, the handle assembly is in the firing state. Rotating the knob 71 pulls the pulling sheet 6 which rotates the indicator 5 in a clockwise direction. The slider 42 slides toward the second section 412 of the sliding slot 41. Squeezing the first handle 1 rotates the second handle 2 counterclockwise, and pushes the staple pushing rod 75 to fire the stapler. After the stapler has been fired, the same reset process as the previous embodiments starts and will not be repeatedly described here.

Because of the distance between the end of the handle and the housing, it is often difficult for the operator to identify whether the stapler has been fired. Therefore, in this embodiment, a rubber nail 78 is further provided on the housing 74 of the stapler. When squeezing the first handle 1, the first end of the first handle 1 nears the rubber nail 78 and can identify to the operator visually that the first end 11 of the first handle 1 is adjacent to the housing 74 of the stapler, and the stapler has been fired.

The above four selected embodiments of the present disclosure can be implemented in combination. For example, combining some features of embodiment 2 and 1 forms a new technical proposal. The combination of some features in embodiment 2, 3 and 4 forms a new technical proposal too. Such combinations of embodiments are within the scope of the present disclosure. In practical applications, other variations and combinations are available and all fall within the scope of the present disclosure. For example, the sliding slot and the slider are not limited to being provided on the first handle, but may also be provided on the second handle, and as such the first handle is provided with a handle abutment. The second handle is provided with a second cavity, and the second end of the first handle is positioned inside the second cavity. When the slider is positioned in the first section of the sliding slot and the first handle is rotated in the first direction, the handle abutment does not engage the slider, the first handle continues to enter the cavity of the second handle, and sets the second handle in the insurance position; The slider is positioned in the second section of the sliding slot, and when the first handle is rotated in the first direction, the handle abutment engages the slider, preventing the first handle from continuing to enter the cavity of the second handle, thereby rotating the second handle from the insurance position to the firing position to fire the stapler.

In addition, the resetting method of the slider is not limited to using a pressure spring. Alternatively, a torsion spring limit portion may be provided between the two sliding portions of the slider, and a slider resetting torsion spring may be provided between the second handle and the torsion spring limit portion. The limit portion of the torsion spring may be a groove, which limits the end of the slider torsion spring. When the slider slides from the first section to the second end of the sliding slot, it compresses and deforms the slider resetting torsion spring. After the squeezing force is released, the slider resetting torsion spring is biased to its initial position.

An embodiment of the present disclosure further provides a stapler, including the abovementioned handle assembly. When the stapler is not ready to be fired, the first handle does not engage the second handle, and the stapler is not fired. The operator can also identify the firing state from the operating experience. Only when the stapler reaches the firing position, the first handle engages the second handle and fire the stapler. In addition to avoiding the accidental firing of the stapler, rupture in the stapler housing is avoided too. Furthermore, the present disclosure includes a shared rotation center for the first handle and the second handle rendering a more compact handle, a smaller opening on the housing provided for the handle, more appealing appearance, yet better structure stability of the stapler.

The handle assembly and the stapler including the handle assembly in the present disclosure have the following advantages:

The present disclosure provides a handle assembly and a stapler including the handle assembly. By having a first handle and a second handle in the assembly, only the movement of the second handle can ultimately fire the stapler in performing cutting and suturing operation; during use, the operator can squeeze the first handle regardless of whether the stapler is ready to be fired. However, when the stapler is not ready to be fired, the first handle will not engage the second handle, and the stapler cannot be fired. Featured with two torsion springs and the two pivot pins, the first handle and the second handle are pivotally attached and can be reset. The first handle and the second handle are rotated around the same rotation center in the invalid state and firing state, rendering enhanced stapler structure stability and improved operator experience.

The detailed description of the present disclosure with reference to specific selected embodiments hereof should not be construed as limiting, but merely as exemplifications of the present disclosure. Those skilled in the art will envision other modifications within the scope and spirit of the claims appended hereto.

What is claimed is:

1. A handle assembly for firing a stapler, comprising:
a first handle and a second handle;
a first pivot pin, fixedly secured to a housing of the stapler and passing through the first handle and the second handle;
a first torsion spring, sleeved on the first pivot, and two ends of the first torsion spring respectively engaged with the housing of the stapler and the second handle;
a handle resetting member, positioned between the first handle and the housing of the stapler, and resetting the first handle when an external force is released;
a sliding slot, disposed on the first handle or the second handle, and comprising a first section and a second section connected with each other;
and a slider, slidably positioned in the sliding slot;
wherein, when the slider is positioned in the first section of the sliding slot, the first handle and the second handle are not linked; when the slider is positioned in the second section of the sliding slot, the first handle and the second handle are linked by the slider.

2. The handle assembly according to claim 1, wherein the sliding slot is positioned on the first handle, and the second handle comprises a handle abutment;
wherein, when the slider is positioned in the first section of the sliding slot and the first handle is rotated in a first direction, the slider is not engaged with the handle abutment, and the second handle remains in an insurance position;
when the slider is positioned in the second section of the sliding slot and the first handle is rotated in the first direction, the slider is engaged with the handle abutment to actuate the second handle from the insurance position to a firing position.

3. The handle assembly according to claim 2, wherein the first handle comprises a first cavity having two side walls; two slots are provided in the two side walls, respectively; the slider comprises two sliding portions and an abutment between the two sliding portions, each sliding portion is slidably positioned in a sliding slot.

4. The handle assembly according to claim 3, wherein a first limit member and a second limit member are provided on each sliding portion and an end of the second section of each slot, respectively; a slider resetting pressure spring is disposed between each first limit member and the corresponding second limit member.

5. The handle assembly according to claim 3, wherein the first handle is provided with an outer housing, and a groove is formed at a position of the outer housing corresponding to the sliding slot; the groove comprises a first section and a second section corresponding to the first section and second section of the sliding slot; a first limit member and a second limit member are provided at each sliding portion and an end of the second section of each groove, respectively; a slider resetting pressure spring is positioned between each first limit member and the corresponding second limit member.

6. The handle assembly according to claim 3, wherein a limit portion for the torsion spring is positioned between the two sliding portions of the slider, and a slider resetting torsion spring is positioned between the limit portion and the second handle.

7. The handle assembly according to claim 3, wherein a first end of the first handle comprises a gripping portion and a second end of the first handle comprises an attachment portion; a first end of the second handle is positioned in a cavity of the attachment portion;
when the slider is positioned in the first section of the sliding slot and the first handle is rotated in the first direction, the second handle continues to enter the cavity of the first handle;
when the slider is positioned in the second section of the sliding slot and the first handle is rotated in the first direction, the slider prevents the second handle from entering the cavity of the first handle.

8. The handle assembly according to claim 1, wherein the handle resetting member comprises a second torsion spring which is sleeved on a second pivot pin; the second pivot pin is fixedly secured to the housing of the stapler, and two ends of the second torsion spring respectively engage the housing of the stapler and the first handle.

9. The handle assembly according to claim 8, wherein the first pivot pin and the second pivot pin are positioned parallel to each other; a first fixing post for fixing an end of the first pivot pin and a second fixing post for fixing an end of the second pivot pin are provided on inner walls on both sides of the housing of the stapler.

10. The handle assembly according to claim 9, wherein a supporting post is provided inside the stapler, two ends of the supporting post are fixed to both sides of the housing of the stapler respectively; a first end of the first torsion spring engages the supporting post, and a second end of the first torsion spring engages the inner wall of the second handle.

11. The handle assembly according to claim 10, wherein a fixing plate is provided between the supporting post and the housing of the stapler; one end of the fixing plate is provided with a curved groove partially wrapping the supporting post, the other end of the fixing plate is fixed to the housing of the stapler;
a first curved portion is further provided on one end of the fixing plate, a holding portion that partially wraps the second torsion spring is provided on a side wall of the fixing plate, a second curved portion is provided on a second end of the first handle, a first end of the second torsion spring engages the first curved portion; and a second end of the second torsion spring is configured to hook the second curved portion.

12. The handle assembly according to claim 1, wherein the handle resetting member comprises a handle resetting pressure spring which is positioned between the first handle and the housing of the stapler.

13. The handle assembly according to claim 12, wherein fixing posts are provided on inner walls on both sides of the housing of the stapler to fix ends of the pivot pins; housing fixing portions are provided on the inner walls of the housings of the stapler; a handle fixing portion is provided on a second end of the first handle, and two ends of the handle resetting pressure spring are fixed to the housing fixing portion and the handle fixing portion respectively.

14. The handle assembly according to claim 13, wherein a supporting post is provided, two ends of which are respectively fixed to both sides of the housing of the stapler, and a first end of the torsion spring engages the supporting post, and a second end of the torsion spring engages the inner wall of the second handle;
a fixing plate is positioned between the supporting post and the housing of the stapler, one end of the fixing plate is provided with a curved groove partially wrapping the supporting post, and the other end of the fixing plate is fixed to the housing of the stapler;
the handle resetting pressure spring is positioned in a cavity formed between the fixing plate and the first handle.

15. The handle assembly according to claim 1, wherein the sliding slot is positioned on the second handle; the first handle comprises a handle abutment;
when the slider is positioned in the first section of the sliding slot and the first handle is rotated in a first direction, the handle abutment does not engage the slider, and the second handle remains in an insurance position;
when the slider is positioned in the second section of the sliding slot and the first handle is rotated in the first direction, the handle abutment engages the slider and rotates the second handle from the insurance position to a firing position.

16. The handle assembly according to claim 1, wherein the position of the slider in the sliding slot is adjusted by an indicator which is movable between a first position area and a second position area;
when the indicator moves from the first position area to the second position area, the slider is actuated to move from the first section to the second section of the sliding slot.

17. The handle assembly according to claim 16, wherein the indicator is attached to a distal end of a pulling sheet, a proximal end of the pulling sheet is sleeved on a screw rod, and a knob is disposed at a distal end of the screw rod;
as the knob is rotated, the pulling sheet is moved towards a proximal end of the stapler, thereby moving the indicator from the first position area to the second position area.

18. The handle assembly according to claim 17, wherein the second handle comprises a pulling sheet abutment;
when the second handle is rotated from the insurance position to the firing position, the pulling sheet abutment engages the pulling sheet so that a hook of the pulling sheet can be disengaged from the indicator.

19. A stapler comprising the handle assembly according to claim 1.

* * * * *